(12) United States Patent
Cheng et al.

(10) Patent No.: US 9,184,396 B2
(45) Date of Patent: Nov. 10, 2015

(54) 6H-INDENO[2,1-B]QUINOLINE DERIVATIVE AND ORGANIC LIGHT EMITTING DIODE USING THE SAME

(71) Applicant: NATIONAL TSING HUA UNIVERSITY, Hsinchu (TW)

(72) Inventors: Chien-Hong Cheng, Hsinchu (TW); Chin-Hsien Chen, Hsinchu (TW); Lun-Chia Hsu, Hsinchu (TW); Yu-Wei Chang, Hsinchu (TW); Ching-Lin Chan, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 282 days.

(21) Appl. No.: 13/913,610

(22) Filed: Jun. 10, 2013

(65) Prior Publication Data

US 2014/0284556 A1  Sep. 25, 2014

(30) Foreign Application Priority Data

Mar. 22, 2013 (TW) .............................. 102110241 A

(51) Int. Cl.
| | | |
|---|---|---|
| *H01L 51/00* | (2006.01) | |
| *C07D 401/14* | (2006.01) | |
| *C07D 221/18* | (2006.01) | |
| *C09K 11/06* | (2006.01) | |
| *H01L 51/50* | (2006.01) | |

(52) U.S. Cl.
CPC .......... *H01L 51/0061* (2013.01); *C07D 221/18* (2013.01); *C07D 401/14* (2013.01); *C09K 11/06* (2013.01); *H01L 51/0072* (2013.01); *C09K 2211/1029* (2013.01); *H01L 51/5012* (2013.01)

(58) Field of Classification Search
None
See application file for complete search history.

(56) References Cited

U.S. PATENT DOCUMENTS

2007/0267958 A1* 11/2007 Kitazawa et al. ............. 313/483
2014/0175383 A1* 6/2014 Yen et al. ....................... 257/40

* cited by examiner

*Primary Examiner* — J. L. Yang
(74) *Attorney, Agent, or Firm* — Rosenberg, Klein & Lee

(57) ABSTRACT

A 6H-indeno[2,1-b]quinoline derivative has a structure of formula (I). Each of $Ar_1$ and $Ar_2$ is a member selected from the group consisting of a substituted or non-substituted aryl group and a substituted or non-substituted heteroaryl group and $R_1$ to $R_9$ are substituents. The 6H-indeno[2,1-b]quinoline derivative of the present invention is provided with thermal stability. Chemical compounds of the present invention are adequate for the materials of the light-emitting layer of an OLED device with high device performance.

14 Claims, 1 Drawing Sheet

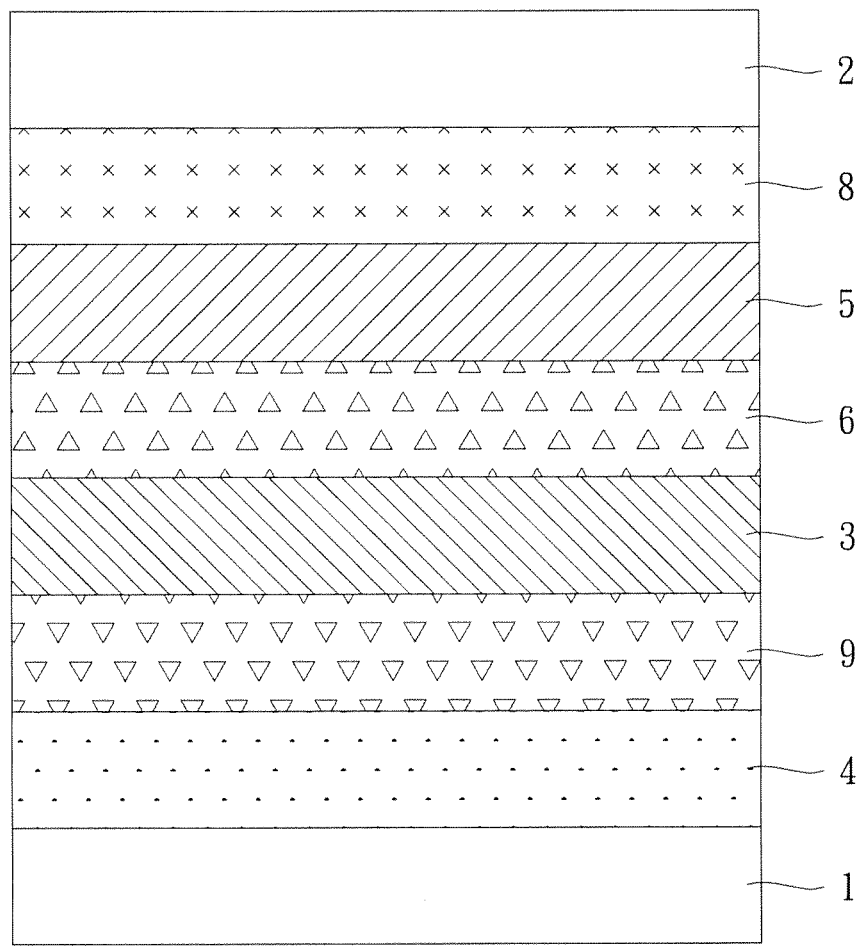

6H-INDENO[2,1-B]QUINOLINE DERIVATIVE AND ORGANIC LIGHT EMITTING DIODE USING THE SAME

BACKGROUND OF THE INVENTION

1. Field of the Invention

The present invention relates to a chemical compound and an organic light emitting diode (OLED), and more particularly to a 6H-indeno[2,1-b]quinoline derivative and organic light emitting diode using the same.

2. Description of the Prior Art

OLED is composed of organic materials and semiconductor materials. OLED works on the mechanism that electrons and holes diffuse through an electron transport layer (ETL) and hole transport layer (HTL) respectively to enter a light-emitting layer, and recombine in the emitting region to form excitons. When excitons fall to the ground state, the energy is given off in the form of photo radiation. The radiation color can be tuned by applying different emitting materials. OLED has been spotlighted due to a lot of advantages, such as self illumination, wider visual angle (>170°), shorter response time (~μs), higher contrast, higher efficiency, lower power consumption, higher brightness, lower operative voltage (3-10V), thinner size (<2 mm), flexibility and so on.

Excitons generated from recombining holes and electrons have triplet state or singlet state for its spin state. Singlet exciton relaxation radiates fluorescence and triplet exciton relaxation radiates phosphorescence. Phosphorescence achieves 3-fold efficiency comparing to fluorescence and may greatly enhance the IQE (internal quantum efficiency) of devices up to 100% by adopting metal complexes in electroluminescent configuration to achieve strong spin-orbital coupling and mixing of singlets and triplets. Therefore, phosphorescent metal complexes are now adopted as phosphorescent dopants in the emitting layer of OLED. In addition, by doping proper materials to the light-emitting layer, self-quenching of the host materials can be reduced greatly to enhance the efficiency of the OLED device. With respect to host materials, they must be capable of catching carriers easily and have high photoelectric conversion performance, high thermal stability and proper band gap of singlet state and triplet state.

To sum up, it is an important issue to develop a novel host material to be applied in OLED.

SUMMARY OF THE INVENTION

It is an object of the present invention to provide a novel chemical compound with high thermal stability to be applied in OLED.

According to one embodiment of the present invention, a 6H-indeno[2,1-b]quinoline derivative has a structure of formula (I):

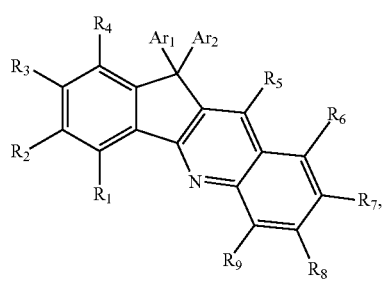

(I)

wherein each of $Ar_1$ and $Ar_2$ is a member selected from the group consisting of a substituted or non-substituted aryl group and a substituted or non-substituted heteroaryl group; each of substituents $R_1$ to $R_9$ is a member independently selected from the group consisting of H, halo, cyano, amino, substituted or non substituted $C_1$-$C_{10}$ alkyl, substituted or non substituted $C_2$-$C_{10}$ alkenyl, substituted or non substituted $C_2$-$C_{10}$ alkynyl, substituted or non substituted $C_3$-$C_{20}$ cycloalkyl, substituted or non substituted $C_3$-$C_{20}$ cycloalkenyl, substituted or non substituted $C_1$-$C_{20}$ heterocycloalkyl, substituted or non substituted $C_1$-$C_{20}$ heterocycloalkenyl, substituted or non substituted aryl and substituted or non substituted heteroaryl.

It is another object of the present invention to provide an organic light emitting diode with high device performance.

According to another embodiment of the present invention, an organic light emitting diode comprising a cathode, an anode and a light-emitting layer arranged between the anode and the cathode. The light-emitting layer comprises the aforementioned 6H-indeno[2,1-b]quinoline derivative.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The FIGURE is a schematic diagram illustrating the structure of an organic light-emitting diode using the 6H-indeno[2,1-b]quinoline derivative.

DESCRIPTION OF THE PREFERRED EMBODIMENT

The 6H-indeno[2,1-b]quinoline derivative has the structure of formula (I) to (IX) according to the present invention:

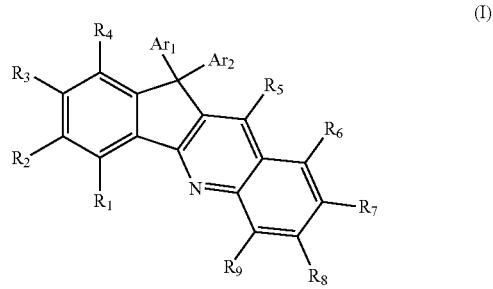

(I)

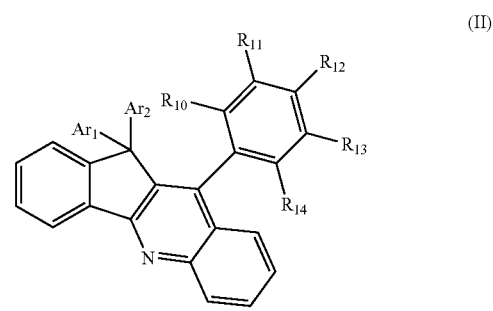

(II)

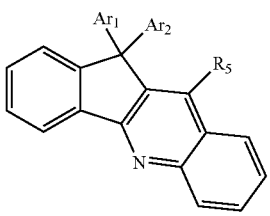
(III)

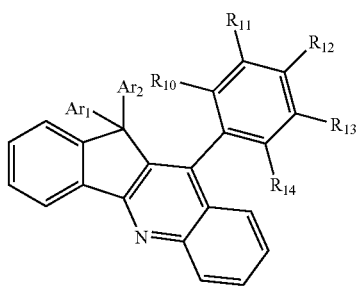
(IV)

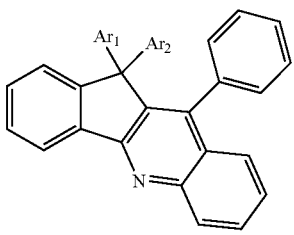
(V)

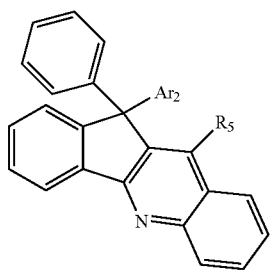
(VI)

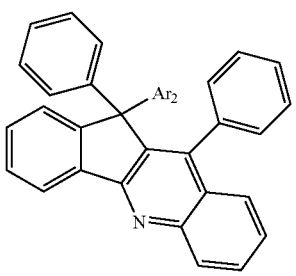
(VII)

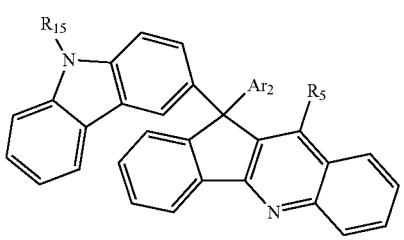
(VIII)

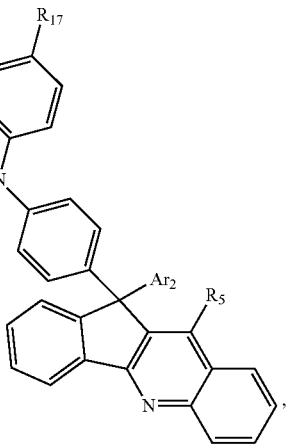
(IX)

wherein each of $Ar_1$ and $Ar_2$ is a member selected from the group consisting of a substituted or non-substituted aryl group and a substituted or non-substituted heteroaryl group; each of substituents $R_1$ to $R_9$ is a member independently selected from the group consisting of H, halo, cyano, amino, substituted or non substituted $C_1$-$C_{10}$ alkyl, substituted or non substituted $C_2$-$C_{10}$ alkenyl, substituted or non substituted $C_2$-$C_{10}$ alkynyl, substituted or non substituted $C_3$-$C_{20}$ cycloalkyl, substituted or non substituted $C_3$-$C_{20}$ cycloalkenyl, substituted or non substituted $C_1$-$C_{20}$ heterocycloalkyl, substituted or non substituted $C_1$-$C_{20}$ heterocycloalkenyl, substituted or non substituted aryl and substituted or non substituted heteroaryl.

The term "aryl" refers to a hydrocarbon moiety having one or more aromatic rings. Examples of aryl moieties include phenyl (Ph), phenylene, naphthyl, naphthylene, pyrenyl, anthryl, and phenanthryl.

The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, heterocycloalkenyl, alkoxy, aryl, aryloxy, heteroaryl, heteroaryloxy, amino, $C_1$-$C_{10}$ alkylamino, dialkylamino, arylamino, diarylamino, $C_1$-$C_{10}$ alkylsulfonamino, arylsulfonamino, alkylimino, arylimino, $C_1$-$C_{10}$ alkylsulfonimino, arylsulfonimino, hydroxyl, halo, thio, alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

TABLE 1
chemical compounds according to embodiments of the present invention.
| NO. | acronym | Chemical formula |
|---|---|---|
| 1 | BPhIDQ | 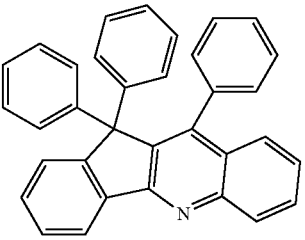 [SMILES: c1ccc(-c2c3c(nc4ccccc24)-c2ccccc2C3(c2ccccc2)c2ccccc2)cc1] |
| 2 | TolCzPhIDQ | 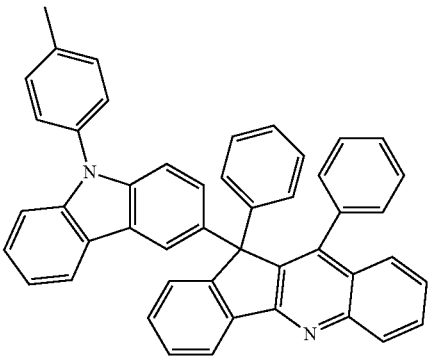 [SMILES: Cc1ccc(-n2c3ccccc3c3cc(C4(c5ccccc5)c5ccccc5-c5nc6ccccc6c(-c6ccccc6)c54)ccc32)cc1] |
| 3 | Tol2NPhPHIDQ | 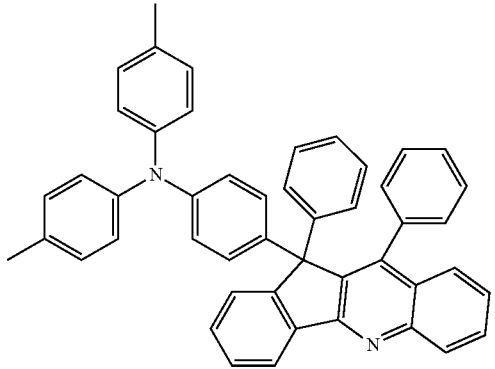 [SMILES: Cc1ccc(N(c2ccc(C)cc2)c2ccc(C3(c4ccccc4)c4ccccc4-c4nc5ccccc5c(-c5ccccc5)c43)cc2)cc1] |
| 4 | BCzIDQ | 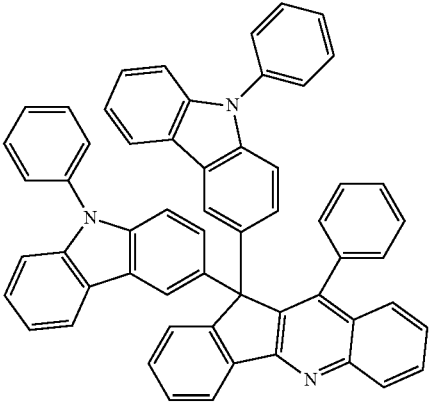 [SMILES: c1ccc(-c2c3c(nc4ccccc24)-c2ccccc2C3(c2ccc3c(c2)c2ccccc2n3-c2ccccc2)c2ccc3c(c2)c2ccccc2n3-c2ccccc2)cc1] |

TABLE 1-continued
chemical compounds according to embodiments of the present invention.
| NO. | acronym | Chemical formula |
|---|---|---|
| 5 | BTPAIDQ | 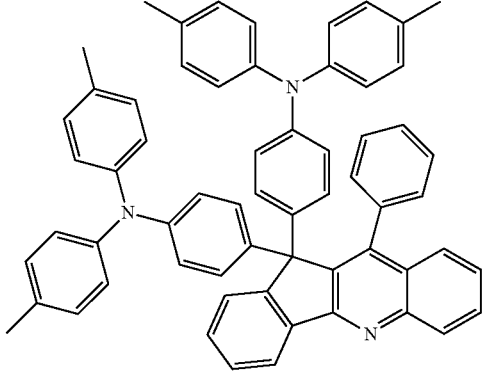 [SMILES: Cc1ccc(N(c2ccc(C)cc2)c2ccc(C3(c4ccc(N(c5ccc(C)cc5)c5ccc(C)cc5)cc4)c4ccccc4-c4nc5ccccc5c(-c5ccccc5)c43)cc2)cc1] |
| 6 | TolCzdiIDQ | 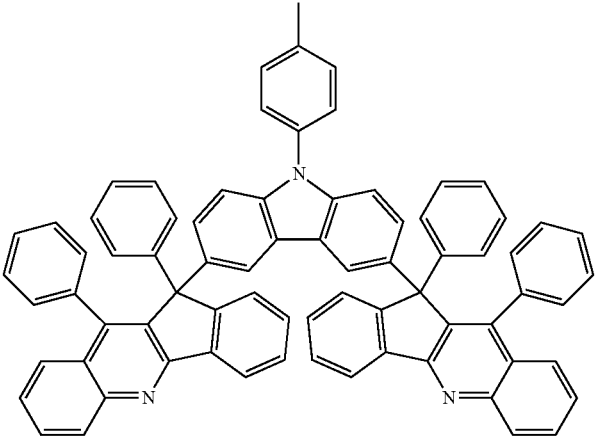 [SMILES: Cc1ccc(-n2c3ccc(C4(c5ccccc5)c5ccccc5-c5nc6ccccc6c(-c6ccccc6)c54)cc3c3cc(C4(c5ccccc5)c5ccccc5-c5nc6ccccc6c(-c6ccccc6)c54)ccc32)cc1] |
| 7 | TolNPh2diIDQ | 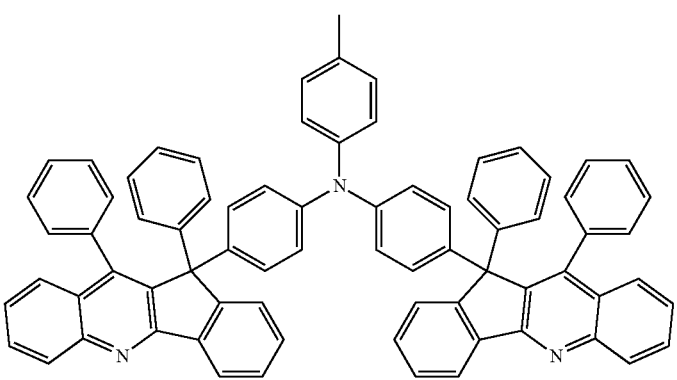 [SMILES: Cc1ccc(N(c2ccc(C3(c4ccccc4)c4ccccc4-c4nc5ccccc5c(-c5ccccc5)c43)cc2)c2ccc(C3(c4ccccc4)c4ccccc4-c4nc5ccccc5c(-c5ccccc5)c43)cc2)cc1] |

Please refer to the following description illustrating the synthetic pathway of the 6H-indeno[2,1-b]quinoline derivatives according to Table 1 of the present invention.

Compound Synthesis

Chemical compounds can be obtained by performing nucleophilic addition reactions twice between starting materials and different aniline aromatic rings (e.g. carbazole or triphenylamine) along with using non-metal catalytic Eaton's reagents on different chemical equivalent basis.

Synthesis of 10-phenyl-11H-indeno[1,2-b]quinolin-11-one

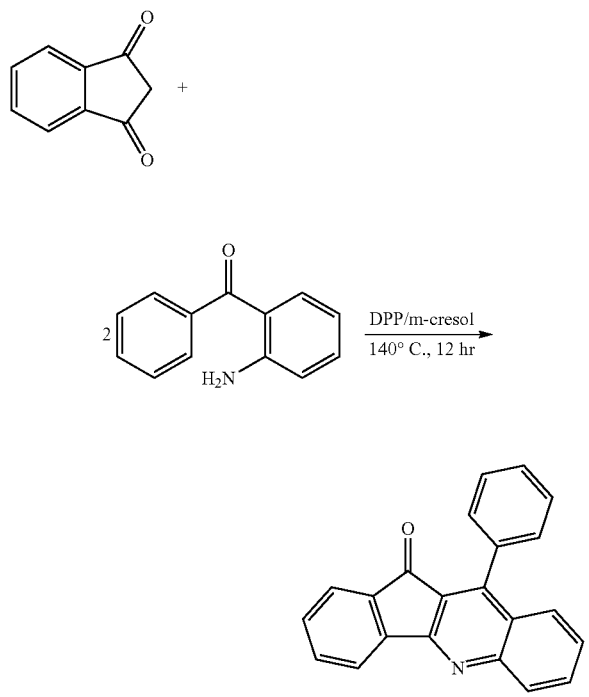

The 6H-indeno[2,1-b]quinoline derivative of the present invention can be synthesized at high percentage yield by performing non-metal catalytic Friedländer reaction to obtain derivatives containing quinolin and ketone. The starting materials 1H-indene-1,3(2H)-dione (307 mg, 1.00 m), 2-amonobenzophenone (400 mg, 2.00 mmol), diphenyl phosphate (DPP, 751 mg, 3.00 mmol) and just-evaporated m-cresol are mixed in a round bottom flask and heated to 140° C. for two hours under nitrogen atmosphere. After reaction, 10% triethylamine/methanol is added into the crude product and then filtered to remove precipitates. Finally, 10-phenyl-11H-indeno[1,2-b]quinolin-11-one, appearing yellow, is separated from the mixture by using column chromatography with N-hexane:ethyl acetate =10:1. The percentage yield is 81.3%. 10-phenyl-11H-indeno[1,2-b]quinolin-11-one obtained here can be also used as starting materials to produce other 6H-indeno[2,1-b]quinoline derivatives.

$^1$H NMR (400 MHz, CDCl$_3$, δ): 7.39-7.50 (m, 4H), 7.54-7.56 (m, 3H), 7.64-7.75 (m, 4H), 8.10-8.15 (m, 2H); $^{13}$C NMR (100 MHz, CDCl$_3$, δ): 121.7, 122.8, 1238, 127.0, 127.7, 128.1, 128.6, 128.9, 129.3, 129.9, 131.6, 131.7, 132.9 135.3 137.5, 143.3, 148.1, 150.4, 162.0, 190.3; HRMS (EI, m/z): [M$^+$] calcd for C$_{22}$H$_{13}$NO, 307.0997. found, 307.1001.

Synthesis of 10-phenyl-11,11-bis(9-phenyl-9H-carbazol-3-yl)-11H-indeno[1,2-b]quinoline

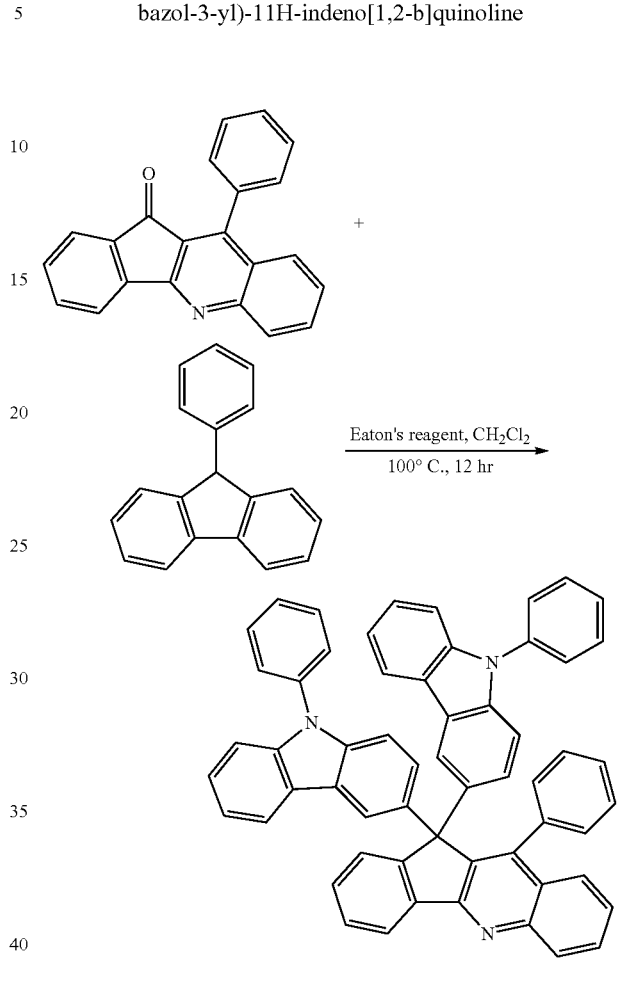

The chemical compound can be obtained by performing nucleophilic addition reactions twice between starting materials and different aniline aromatic rings (e.g. carbazole or triphenylamine) along with using non-metal catalytic Eaton's reagents on different chemical equivalent basis. First, 10-phenyl-11H-indeno[1,2-b]quinolin-11-one (860 mg, 2.80 mmol) and 9-phenyl-9H-carbazole (1500 mg, 6.10 mmol) are placed in a round bottom flask and then dissolved in 5 ml of dichloromethane. Subsequently, 800 μl of Eaton's reagent is slowly dripped into the flask to promote reaction. After 12 hours of reaction at 100° C., the crude product is extracted with 20 ml of dichloromethane and sodium bicarbonate for three times. Finally, an organic layer of the crude product is dehydrated with magnesium sulfate and concentrated to be sublimated and purified to obtain 1820 mg of 10-phenyl-11,11-bis(9-phenyl-9H-carbazol-3-yl)-11H-indeno[1,2-b]quinoline. The percentage yield is 83.8%.

$^1$H NMR (400 MHz, CDCl$_3$, δ): 6.59 (d, 1H, J=7.6 Hz), 6.82 (dd, 2H, J=7.6, 7.2 Hz), 7.04-7.18 (m, 4H), 7.22-7.26 (m, 1H), 7.28-7.46 (m, 6H), 7.52-7.59 (m, 4H), 7.67-7.73 (m, 2H), 7.79 (d, 1H, J=7.6 Hz), 8.27 (d, 1H. J=8.0 Hz), 8.33 (d, 1H, J=7.2 Hz); $^{13}$C NMR (100 MHz, CDCl$_3$, δ): 64.1, 109.0, 109.7, 119.7, 120.6, 120.9, 121.9, 122.7, 123.4, 125.6, 125.7, 125.8, 126.5, 126.8, 127.1, 127.3, 127.4, 127.5, 127.7, 128.6, 128.9, 129.1, 129.7, 129.8, 131.2, 135.0, 135.2, 137.7, 137.9, 139.5, 141.0, 141.5, 145.2, 148.6, 157.2, 161.0; HRMS (EI, m/z): [M+] calcd for $C_{58}H_{37}N_3$, 775.2987. found, 775.2993. Anal. calcd. for $C_{58}H_{37}N_3$: C, 89.78; H, 4.81; N, 5.42. found: C, 89.22; H, 4.99; N, 5.46.

Synthesis of 4,4'-(10-phenyl-11H-indeno[1,2-b]quinoline-11,11-diyl)bis(N,N-di-p-tolylaniline

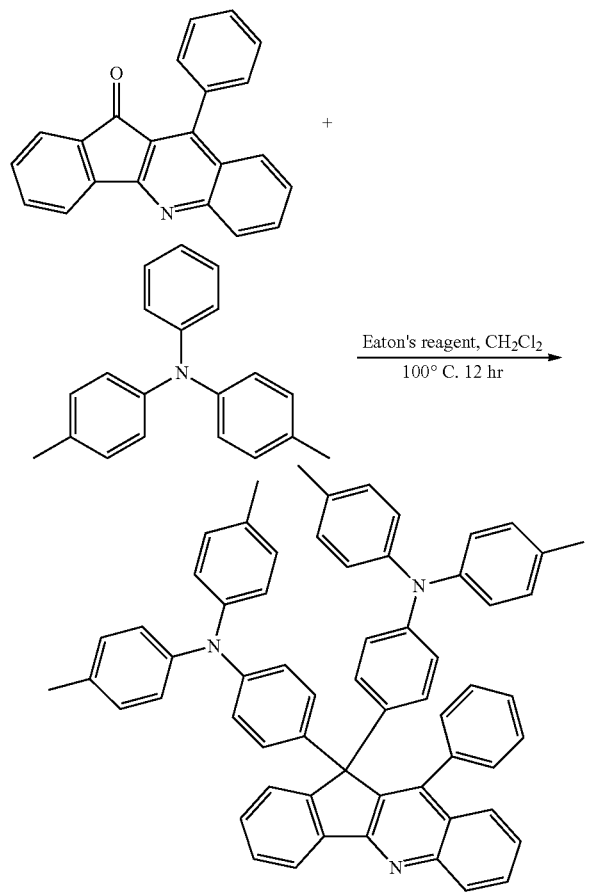

Referring to the reaction formula above, 10-phenyl-11H-indeno[1,2-b]quinolin-11-one (860 mg, 2.80 mmol) and 4-methyl-N-phenyl-N-(p-tolyl)aniline (1668 mg, 6.10 mmol) are placed in a round bottom flask and then dissolved in 5 ml of dichloromethane. Subsequently, 800 µl of Eaton's reagent is slowly dripped into the flask to promote reaction. After 12 hours of reaction at 100° C., the crude product is extracted with 20 ml of dichloromethane and sodium bicarbonate for three times. Finally, an organic layer of the crude product is dehydrated with magnesium sulfate and concentrated to be sublimated and purified to obtain 2050 mg of 10-phenyl-11,11-bis(9-phenyl-9H-carbazol-3-yl)-11H-indeno[1,2-b]quinoline. The percentage yield is 87.6%.

$^1$H NMR (400 MHz, CDCl$_3$, δ): 2.26 (s, 12H), 6.63-6.75 (m, 10H), 6.90 (d, 8H, J=8.0 Hz), 7.00 (d, 8H, J=7.6 Hz), 7.15 (dd, 2H, J=8.0, 7.6 Hz), 7.26-7.35 (m, 4H), 7.36 (dd, 1H, J=7.6, 7.2 Hz), 7.42 (dd, 1H, J=8.0, 7.2 Hz), 7.66 (ddd, 1H, J=7.6, 7.2, 0.8 Hz), 8.20 (d, 1H, J=7.6 Hz), 8.25 (d, 1H, J=7.2 Hz); $^{13}$C NMR (100 MHz, CDCl$_3$, δ): 20.7, 62.8, 121.8, 122.0, 124.2, 125.6, 126.4, 127.4, 127.5, 127.6, 128.5, 129.0, 129.5, 129.7, 130.1, 131.1, 132.2, 135.2, 136.1, 138.0, 141.0, 144.5, 145.3, 146.3, 148.5, 156.2, 160.7; FIRMS (EI, m/z): [M+] calcd for $C_{61}H_{47}N_3$, 835.3926. found, 835.3934. Anal. calcd. for $C_{61}H_{47}N_3$: C, 89.13; H, 5.76; N, 5.11; found: C, 89.42; H, 5.75, N, 4.71.

Synthesis of 10,11-diphenyl-11H-indeno[1,2-b]quinolin-11-ol

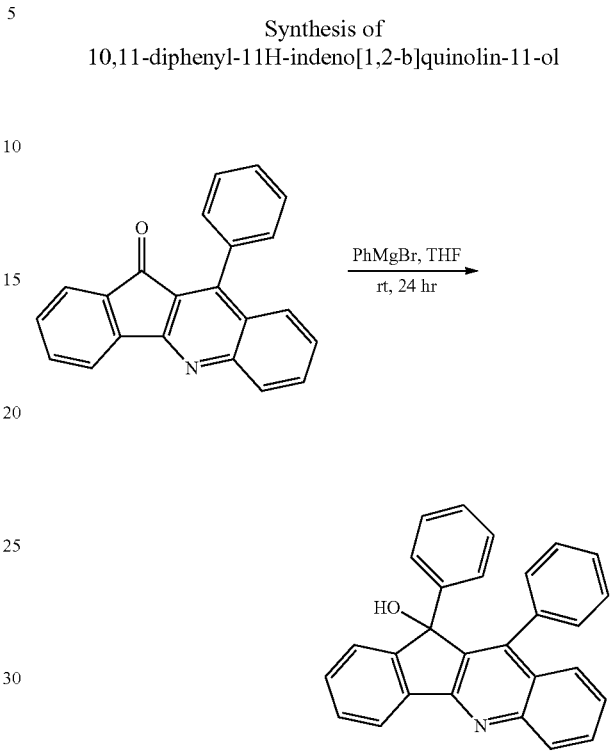

After dripping 1M phenylmagnesium bromide (20 ml, 20.0 mmol) into the starting material 10-phenyl-1H-indeno[1,2-b]quinolin-11-one (3.07 g, 10.0 mmol) which is dissolved in pure tetrahydrofuran, the mixed solution undergoes reaction for 24 hours at room temperature. Then, the reaction is terminated by adding ammonium chloride solution therein. Finally, 3.47 g of 10,11-diphenyl-11H-indeno[1,2-b]quinolin-11-ol is obtained by filtering the mixed solution to remove precipitates. The percentage yield is 90.0%. 10-diphenyl-11H-indeno[1,2-b]quinolin-11-ol obtained here can be also used as starting materials to produce other 6H-indeno[2,1-b]quinoline derivatives.

HRMS (EI, m/z): [M+] calcd for $C_{28}H_{19}NO$, 385.1467. found, 385.1472.

Synthesis of 10,11-diphenyl-11-(9-(p-tolyl)-9H-carbazol-3-yl)-11H-indeno[1,2-b]quinoline

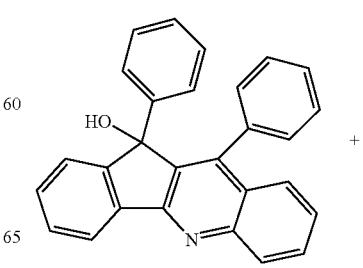

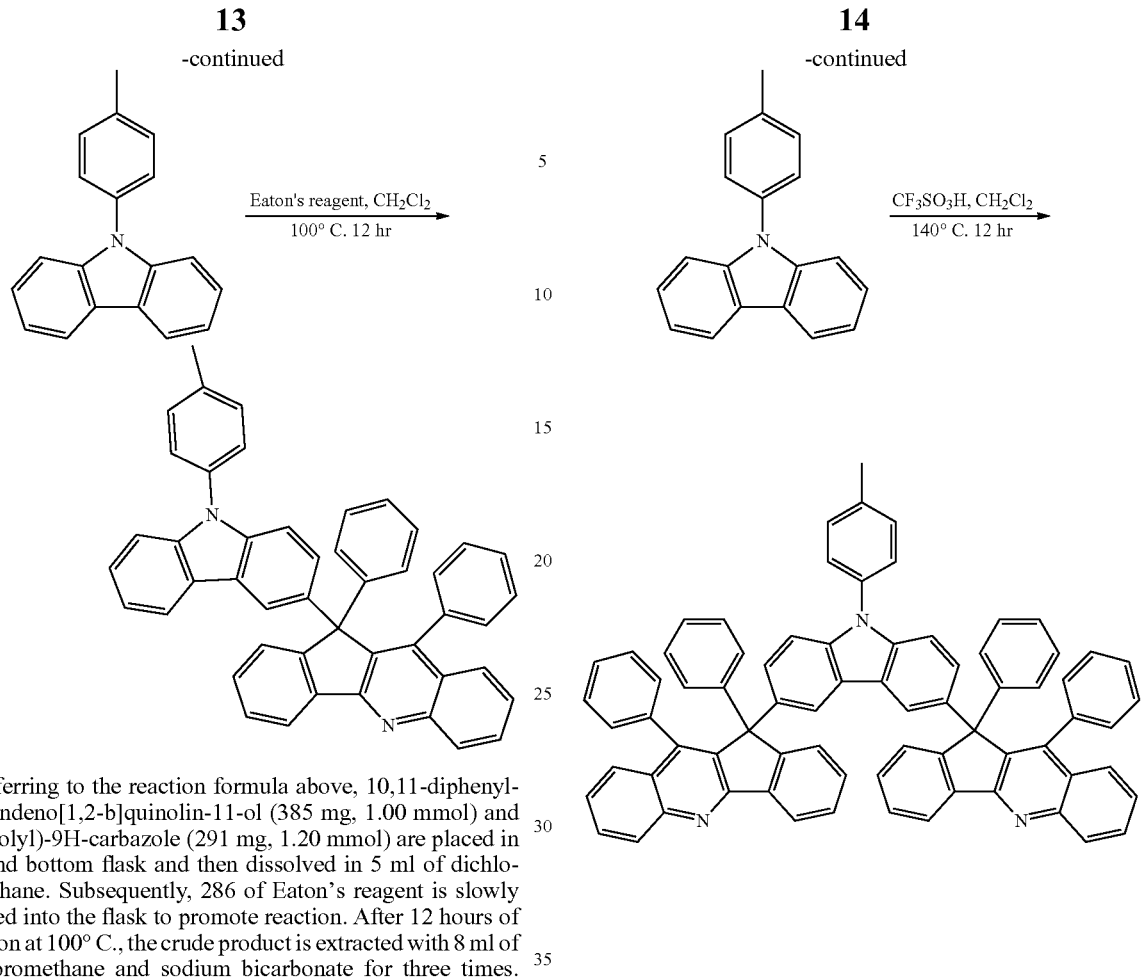

Referring to the reaction formula above, 10,11-diphenyl-11H-indeno[1,2-b]quinolin-11-ol (385 mg, 1.00 mmol) and 9-(p-tolyl)-9H-carbazole (291 mg, 1.20 mmol) are placed in a round bottom flask and then dissolved in 5 ml of dichloromethane. Subsequently, 286 of Eaton's reagent is slowly dripped into the flask to promote reaction. After 12 hours of reaction at 100° C., the crude product is extracted with 8 ml of dichloromethane and sodium bicarbonate for three times. Finally, an organic layer of the crude product is dehydrated with magnesium sulfate and concentrated to be sublimated and purified to obtain 521 mg of 10,11-diphenyl-11-(9-(p-tolyl)-9H-carbazol-3-yl)-11H-indeno[1,2-b]quinoline. The percentage yield is 83.4%.

$^1$H NMR (400 MHz, CDCl$_3$, δ): 2.44 (s, 3H), 6.55 (d, 1H, J=8.0 Hz). 6.69 (d, 1H, J=7.6 Hz), 6.83 (dd, 1H, J=7.6, 7.2 Hz), 7.25-7.47 (m. 20H), 7.60 (d, 1H, J=1.2 Hz), 7.70 (ddd, 1H, J=8.4, 7.6, 20 Hz), 7.81 (d, 1H, J=7.6 Hz), 8.29 (d, 1H, J=8.4 Hz), 8.34 (d, 1H, J=7.6 Hz); $^{13}$C NMR (100 MHz, CDCl$_3$, δ): 21.2, 64.0, 108.9, 109.7, 129.5, 120.5, 120.9, 121.9, 122.5, 123.2, 125.6, 125.7, 126.4, 126.5, 126.6, 126.9, 127.3, 127.4, 127.5, 127.6, 127.7, 128.5, 128.8, 128.9, 129.1, 129.6, 129.7, 130.4, 131.2, 134.2, 134.9, 135.0, 137.2, 138.0, 139.6, 141.0, 141.2, 143.8, 145.1, 148.6, 156.7, 160.8; HRMS (EI, m/z): [M$^+$] calcd for C$_{47}$H$_{32}$N$_2$, 624.2565; found, 624.2557. Anal. calcd. for C$_{47}$H$_{32}$N$_2$: C, 90.35; H, 5.16; N, 4.48; found: C, 89.85; H, 5.49; N, 4.11.

Synthesis of 11,11'-(9-(p-tolyl)-9H-carbazole-3,6-diyl)bis(10,11-diphenyl-11H-indeno[1,2-b]quinoline

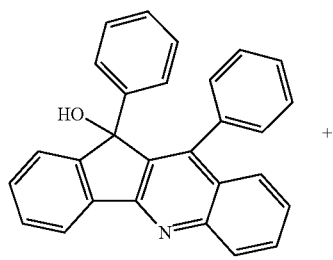

+

The products of the present invention can be obtained via the reaction between starting materials and different aniline aromatic rings. In an embodiment, the starting material 10,11-diphenyl-1H-indeno[1,2-b]quinolin-11-ol (963 mg, 2.50 mmol) and 9-(p-tolyl)-9H-carbazole (257 mg, 1.00 mmol) are placed in a round bottom flask and then dissolved in 10 ml of dichloromethane. Subsequently, trifluoromethanesulfonic acid (0.27 ml, 3.0 mmol) is slowly dripped into the flask to promote reaction. After 12 hours of reaction at 140° C., the crude product is extracted with 50 ml of Ethyl acetate and sodium bicarbonate for three times. Finally, an organic layer of the crude product is dehydrated with magnesium sulfate and concentrated to be sublimated and purified to obtain 670 mg of 11,11'-(9-(p-tolyl)-9H-carbazole-3,6-diyl)bis(10,11-diphenyl-11H-indeno[1,2-b]quinoline. The percentage yield is 67.6%.

$^1$H NMR (400 MHz, CDCl$_3$, δ): 2.41 (s, 3H), 6.46-6.52 (m, 3H), 6.60 (d, 1H, J=6.0 Hz), 6.73-682 (m, 4H), 6.87-7.10 (m, 17H), 7.19-7.35 (m, 14H), 7.39-7.45 (m, 2H), 7.65-7.70 (m, 2H), 8.22-8.33 (m, 3H); $^{13}$C NMR (100 MHz, CDCl$_3$, δ): 21.1, 63.9, 108.7, 108.9, 120.9, 121.0, 121.8, 122.4, 122.5, 125.6, 125.7, 126.3, 126.4, 126.5, 126.8, 126.9, 127.2, 127.3, 127.3, 127.4, 127.5, 127.7, 127.8, 128.4, 128.5, 128.7, 128.8, 128.9, 129.2, 129.5, 129.6, 139.9, 139.3, 139.3, 131.2, 131.3, 133.7, 134.0, 134.7, 134.8, 134.9, 135.0, 137.1, 138.0, 139.7, 139.8, 140.9, 141.0, 143.7, 143.9, 145.1, 145.2, 148.5, 156.6, 156.7, 160.6, 160.7; HRMS (EI, m/z): [M$^+$] calcd for $C_{75}H_{49}N_3$, 991.3926; found, 991.3933. Anal. calcd. for $C_{75}H_{49}N_3$: C, 90.79; H, 4.98; N, 4.23; found: C, 90.30; H, 4.69; N, 4.23.

Synthesis of 4-(10,11-diphenyl-11H-indeno[1,2-b]quinolin-11-yl)-N,N-di-p-tolylaniline

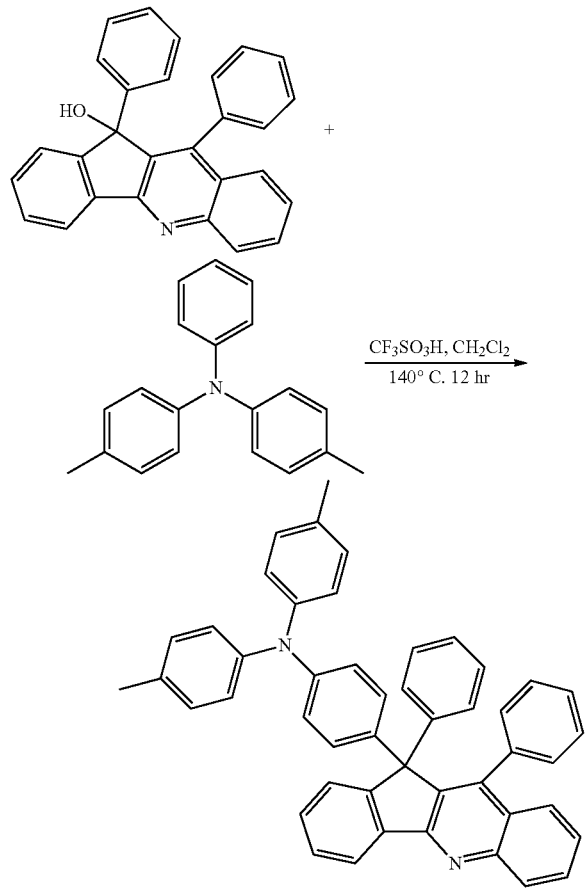

In an embodiment, the starting material 10,11-diphenyl-11H-indeno[1,2-b]quinolin-11-ol (385 mg, 1.00 mmol) and 4-methyl-N-phenyl-N-(p-tolyl)aniline (328 mg, 1.20 mmol) are placed in a round bottom flask and then dissolved in 10 ml of dichloromethane. Subsequently, trifluoromethanesulfonic acid (0.13 ml, 1.50 mmol) is slowly dripped into the flask to promote reaction. After 12 hours of reaction at 140° C., the crude product is extracted with 50 ml of Ethyl acetate and sodium bicarbonate for three times. Finally, an organic layer of the crude product is dehydrated with magnesium sulfate and concentrated to be sublimated and purified to obtain 575 mg of 4-(10,11-diphenyl-11H-indeno[1,2-b]quinolin-11-yl)-N,N-di-p-tolylaniline. The percentage yield is 89.7%.

$^1$H NMR (400 MHz, CDCl$_3$, δ): 2.66 (s, 6H), 6.59-6.70 (m, 61-1), 6.97 (d, 4H, J=7.6 Hz), 7.20-7.26 (m, 10H), 7.28-7.46 (m, 7H), 7.68 (dd, 1H, J=6.8, 2.0 Hz), 8.22 (d, 1H, J=8.4 Hz), 8.26 (d, 1H, J=7.6 Hz); $^{13}$C NMR (100 MHz, CDCl$_3$, δ): 20.8, 63.3, 121.8, 121.9, 124.2, 125.6, 125.7, 126.4, 127.5, 127.6, 127.7, 127.8, 128.4, 128.6, 129.0, 129.1, 129.5, 129.6, 129.7, 130.0, 131.1, 132.2, 135.1, 135.7, 138.0, 140.8, 143.4, 144.8, 145.3, 146.3, 148.6, 156.2, 160.7; HRMS (EI, m/z): [M$^+$] calcd for $C_{48}H_{36}N_2$, 640.2878; found: 640.2880. Anal. calcd. for $C_{48}H_{36}N_2$: C, 89.97; H, 5.66; N, 4.37; found: C, 89.70; H, 5.42; N, 3.98.

Syntehsis of 4-(10,11-diphenyl-11H-[1,2-b]quinolin-11-yl)-N-(4-(10,11-diphenyl-11H-indeno[1,2-b]quinolin-11-yl)phenyl)-N-(p-tolyl)aniline

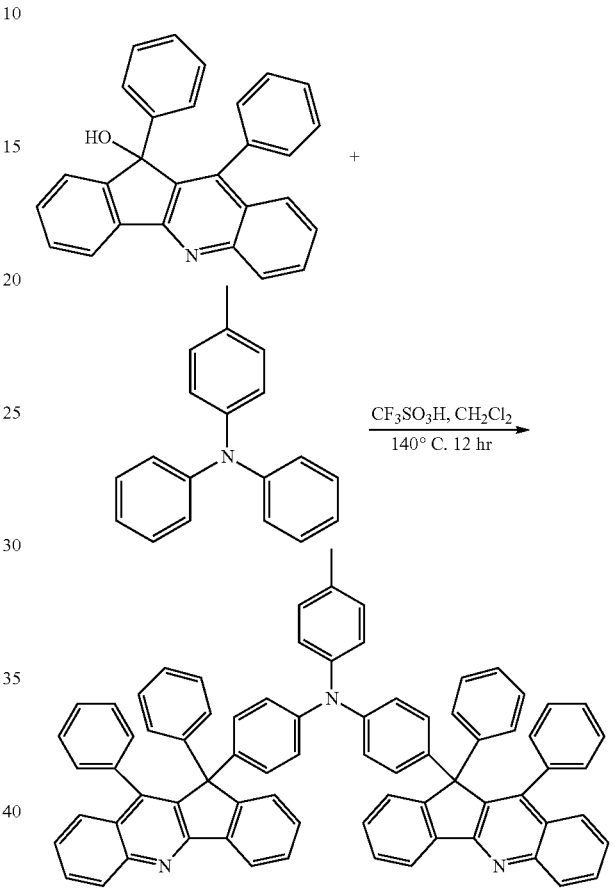

In an embodiment, the starting material 10,11-diphenyl-11H-indeno[1,2-b]quinolin-11-ol (385 mg, 2.50 mmol) and 4-methyl-N,N-diphenylaniline (259 mg, 1.00 mmol) are placed in a round bottom flask and then dissolved in 10 ml of dichloromethane. Subsequently, trifluoromethanesulfonic acid (0.27 ml, 3.00 mmol) is slowly dripped into the flask to promote reaction. After 12 hours of reaction at 140° C., the crude product is extracted with 50 ml of Ethyl acetate and sodium bicarbonate for three times. Finally, an organic layer of the crude product is dehydrated with magnesium sulfate and concentrated to be sublimated and purified to obtain 699 mg of 4-(10,11-diphenyl-11H-[1,2-b]quinolin-11-yl)-N-(4-(10,11-diphenyl-11H-indeno[1,2-b]quinolin-11-yl)phenyl)-N-(p-tolyl)aniline. The percentage yield is 70.3%.

$^1$H NMR (400 MHz, CDCl$_3$, δ): 6.66 (d, 2H, J=7.6 Hz), 6.99 (d, 4H, J=8.0 Hz), 7.05-7.17 (m, 7H), 7.27-7.40 (m, 4H, J=7.2 Hz), 7.48 (t, 1H), 7.72 (dd, 1H, J=8.0, 6.4 Hz), 8.33 (d, 1H, J=7.6 Hz), 8.38 (d, 1H, J=7.6 Hz); $^{13}$C NMR (100 MHz, CDCl$_3$, δ): 20.8, 63.3, 121.9, 122.4, 122.5, 123.4, 124.5, 125.6, 125.7, 126.4, 127.4, 127.5, 127.6, 128.1, 128.4, 128.5, 128.6, 128.7, 129.0, 129.2, 129.6, 129.7, 129.8, 129.0, 130.0, 131.2, 132.5, 132.6, 135.0, 135.1, 136.2, 137.9, 140.7, 143.2, 143.3, 144.9, 146.0, 148.6, 156.0, 156.1, 160.7; HRMS (EI, m/z): [M+] calcd for $C_{75}H_{51}N_3$, 993.4083; found, 993.4075. Anal. calcd. for $C_{75}H_{51}N_3$: C, 90.60; H, 5.17; N, 4.23; found: C, 86.82; H, 5.29; N, 408.

Synthesis of
(10,11,11-triphenyl-11H-indeno[1,2-b]quinoline

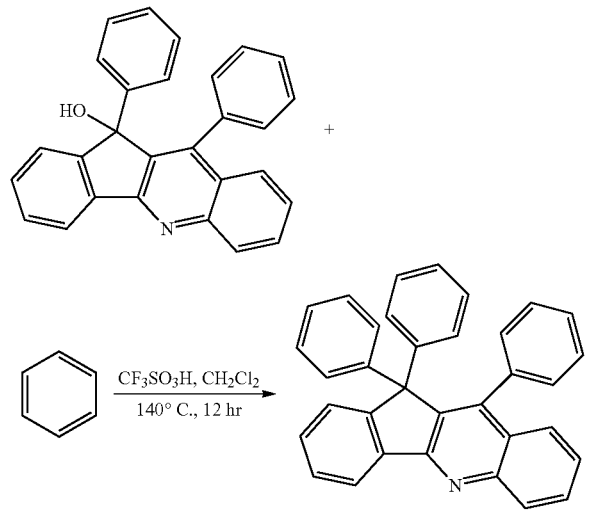

In all embodiment, the starting material 10,11-diphenyl-11H-indeno[1,2-b]quinolin-11-ol (385 mg, 2.50 mmol) and benzene (1430 mg, 18.31 mmol) are placed in a round bottom flask and then dissolved in 10 ml of dichloromethane. Subsequently, trifluoromethanesulfonic acid (0.09 ml, 1.10 mmol) is slowly dripped into the flask to promote reaction. After 12 hours of reaction at 140° C., the crude product is extracted with 50 ml of Ethyl acetate and sodium bicarbonate for three times. Finally, an organic layer of the crude product is dehydrated with magnesium sulfate and concentrated to be sublimated and purified to obtain 281 mg of 10,11,11-triphenyl-11H-indeno[1,2-b]quinoline. The percentage yield is 91.7%.

$^1$H NMR (400 MHz, CDCl$_3$, δ): 6.57 (d, 2H, J=6.8 Hz), 6.88-6.91 (m, 4H), 6.99-7.12 (m, 9H), 7.21-7.25 (m, 2H), 7.28-7.36 (m, 2H), 7.40-7.44 (m, 1H), 7.64-7.70 (m, 1H), 8.22 (d, 1H, J=7.6 Hz), 8.27 (d, 1H, J=7.6 Hz); $^{13}$C NMR (100 MHz, CDCl$_3$, δ): 6.38, 121.9, 125.5, 125.7, 126.4, 127.2, 127.3, 127.6, 127.8, 128.4, 128.5, 128.7, 129.0, 129.2, 129.6, 131.2, 135.0, 138.1, 140.4, 143.0, 145.0, 148.6, 156.0, 160.7; HRMS (EI, m/z): [M+] calcd for $C_{34}H_{23}N$, 445.1830. found, 445.1825. Anal. calcd. for $C_{34}H_{23}N$: C, 91.65; H, 5.20; N, 3.14; found: C, 91.50; H, 5.15; N, 2.72.

TABLE 2 properties of host materials using
6H-indeno[2,1-b]quinoline derivatives.

| host materials | $T_g$ (° C.) | $T_d$ (° C.) | $E_g$ (eV) | $E_T$ (eV) |
|---|---|---|---|---|
| CBP | 62 | 373 | 3.40 | 2.56 |
| BPhIDQ | 91 | N/A | 3.53 | 2.58 |
| BCzIDQ | 198 | N/A | 3.30 | 2.58 |
| BTPAIDQ | 151 | N/A | 3.17 | 2.58 |
| TolCzPhIDQ | 154 | N/A | 3.50 | 2.58 |

TABLE 2-continued properties of host materials using
6H-indeno[2,1-b]quinoline derivatives.

| host materials | $T_g$ (° C.) | $T_d$ (° C.) | $E_g$ (eV) | $E_T$ (eV) |
|---|---|---|---|---|
| Tol2NPhPhIDQ | 133 | N/A | 3.25 | 2.58 |
| TolCzdiIDQ | 218 | N/A | 3.25 | 2.58 |
| TolNPh$_2$diIDQ | 196 | N/A | 3.10 | 2.58 |

$T_g$: Glass transition temperature
$T_d$: Decomposition Temperature
$E_g$: Energy gap
$E_T$: Triplet energy The Table 2 displays properties of host materials using 6H-indeno[2,1-b]quinoline derivatives except that CBP(4,4'-Bis(N-carbazolyl)-1,1'-biphenyl) is a control group. Comparing to CBP, the 6H-indeno[2,1-b]quinoline derivatives of the present invention have higher glass transition temperature ($T_g$) and thus have high thermal stability. Besides, different charge transport moieties can be incorporated into the chemical compounds of the present invention without changing its triplet state (approx. 2.58 eV), which can be applied to red, orange or green emitting devices.

Besides, referring to the FIG., the FIG. is a schematic diagram illustrating the structure of the organic light emitting diode using the 6H-indeno[2,1-b]quinoline derivative as host materials according to an embodiment of the present invention. The organic light emitting diode comprises an anode 1, a cathode 2 and a light-emitting layer 3 arranged between the anode 1 and the cathode 2. The light-emitting layer 3 comprises the chemical compounds provided by the present invention and is formed by doping light emitting materials into the host materials. The structure of the light-emitting materials also comprises a hole transport layer 4, an electron blocking layer 9, an light-emitting layer 3, a hole blocking layer 6, an electron transporting layer 5 and an electron injection layer 8 formed sequentially from bottom to top on the anode 1. Thickness of each layer displayed in the FIGURE is not representative of actual size. Among these layers, the electron blocking layer 9, the hole blocking layer 6, and the electron injection layer 8 are optionally involved. The 6H-indeno[2,1-b]quinoline derivative of the present invention can be used as host materials or dopant of the light emitting layer 3.

For example, the organic light emitting diode of the present invention can be a red phosphorescent OLED, a green phosphorescent OLED or a orange phosphorescent OLED.

Exemplified Electroluminescent Device Structure

Light emitting devices using different materials are exemplified here for testing and comparing properties thereof. Among these devices, ITO is used as substrates; electrode materials comprises LiF/Al; light-emitting materials comprises Ir(piq)$_3$(Iridium(III)tris(1-phenyl-isoquinolinato-C2,N), Ir(ppy)$_3$(Iridium(III)Tris[2-phenylpyridinato-C2,N]), Ir(pq)$_3$(Iridium(III)tris[2-phenyl)-'C(quinolinyl-'N)); the electron transport layer comprises BCP(2,9-dimethyl-4,7-diphenyl-[1,10]phenanthroline) and Alq3 (tris(8-hydroxyquinoline)aluminum(III), which are also adequate for electron blocking layer or for both; hole transport layer comprises NPB (4,4'-bis[N-(1-naphthyl)-N-phenyl-amino]biphenyl) and TCTA (4,4',4''-tri(N-carbazolyl)triphenylamine)), which are also adequate for electron blocking layer or for both.

Comparison Between Device Performance

TABLE 3 properties of green OLED. (device configuration:
NPB (20)/TCTA (10)/7% Ir (ppy)$_3$: Host material (30)/BCP (10)/Alq (40)/LiF (1))

| Device | $V_d^{*a}$ [V] | $\eta_{ext}^{*b}$ [%, V] | $L^{*c}$ [cd/m$^2$, V] | $\eta_c^{*d}$ [cd/A, V] | $\eta_p^{*e}$ [lm/W, V] | $\lambda_{em}^{*f}$ [nm] | CIE, 8V (x, y) |
|---|---|---|---|---|---|---|---|
| CBP | 2.8 | 22.9, 4.5 | 163089, 15.5 | 64.7, 4.5 | 64.2, 3.0 | 586 | (0.56, 0.44) |
| BCzIDQ | 2.8 | 25.8, 3.0 | 118075, 17.0 | 68.4, 3.0 | 71.7, 3.0 | 588 | (0.57, 0.43) |
| BTPAIDQ | 2.3 | 17.2, 3.5 | 67583, 15.0 | 44.2, 3.5 | 53.4, 2.5 | 588 | (0.57, 0.43) |
| TolCzPhIDQ | 2.7 | 21.5, 3.5 | 88155, 17.5 | 58.6, 3.5 | 60.2, 3.0 | 584 | (0.58, 0.44) |
| Tol2NPhPhIDQ | 2.5 | 16.7, 5.5 | 112054, 15.0 | 50.3, 5.5 | 38.2, 3.5 | 580 | (0.54, 0.45) |
| TolCzdiIDQ | 3.2 | 26.2, 5.0 | 93286, 18.0 | 67.9, 5.5 | 48.9, 4.0 | 590 | (0.57, 0.43) |

*$^a$V$_d$: drive voltage
*$^b$η$_{ext}$: maximum external quantum efficiency
*$^c$L: maximum luminescence
*$^d$η$_c$: maximum current efficiency
*$^e$η$_p$: maximum power efficiency
*$^f$λ$_{em}$: maximum emission wavelength

TABLE 4 properties of orange OLED. (device configuration:
NPB (20)/TCTA (10)/4% Ir (pq)3: host material (30)/BCP (15)/Alq (50)/LiF (1))

| Device | Vd [V] | $\eta_{ext}$ [%, V] | L [cd/m$^2$, V] | $\eta_c$ [cd/A, V] | $\eta_p$ [lm/W, V] | $\lambda_{em}$ [nm] | CIE, 8V (x, y) |
|---|---|---|---|---|---|---|---|
| CBP | 2.8 | 22.9, 4.5 | 163089, 15.5 | 64.7, 4.5 | 64.2, 3.0 | 586 | (0.56, 0.44) |
| BCzIDQ | 2.8 | 25.8, 3.0 | 118075, 17.0 | 68.4, 3.0 | 71.7, 3.0 | 588 | (0.57, 0.43) |
| BTPAIDQ | 2.3 | 17.2, 3.5 | 67583, 15.0 | 44.2, 3.5 | 53.4, 2.5 | 588 | (0.57, 0.43) |
| TolCzPhIDQ | 2.7 | 21.5, 3.5 | 88155, 17.5 | 58.6, 3.5 | 60.2, 3.0 | 584 | (0.58, 0.44) |
| Tol2NPhPhIDQ | 2.5 | 16.7, 5.5 | 112054, 15.0 | 50.3, 5.5 | 38.2, 3.5 | 580 | (0.54, 0.45) |
| TolCzdiIDQ | 3.2 | 26.2, 5.0 | 93286, 18.0 | 67.9, 5.5 | 48.9, 4.0 | 590 | (0.57, 0.43) |

TABLE 5 properties of red OLED. (device configuration:
NPB (20)/TCTA (10)/4% Ir (piq)3: host material (30)/BCP (15)/Alq (50)/LiF (1))

| Device | Vd [V] | $\eta_{ext}$ [%, V] | L [cd/m$^2$, V] | $\eta_c$ [cd/A, V] | $\eta_p$ [lm/W, V] | $\lambda_{em}$ [nm] | CIE, 8V (x, y) |
|---|---|---|---|---|---|---|---|
| CBP | 3.1 | 18.2, 5.0 | 56041, 15.0 | 24.6, 5.0 | 21.5, 3.5 | 620 | (0.66, 0.34) |
| BCzIDQ | 3.1 | 24.3, 3.5 | 53322, 17.5 | 30.4, 3.5 | 27.3, 3.5 | 620 | (0.67, 0.33) |
| BTPAIDQ | 2.6 | 18.7, 5.0 | 47469, 15.0 | 23.7, 5.0 | 23.0, 3.0 | 618 | (0.67, 0.33) |
| TolCzPhIDQ | 3.0 | 23.4, 3.0 | 44574, 19.5 | 33.5, 3.0 | 35.0, 3.5 | 616 | (0.66, 0.34) |
| Tol2NPhPhIDQ | 2.6 | 17.2, 5.5 | 57032, 14.0 | 23.2, 5.5 | 18.7, 3.0 | 618 | (0.66, 0.34) |
| TolCzdiIDQ | 3.2 | 23.4, 4.0 | 40921, 17.0 | 26.6, 4.0 | 23.6, 3.5 | 622 | (0.67, 0.33) |

TABLE 6 properties of green OLED. (device configuration: NPNPB
60/NPB (10)/TCTA (10)/7% Ir (ppy)3: host material (30)/BAlq (30)/LiF (1))

| Device | L, 10V [cd/m$^2$] | $\eta_{ext}$ [%, 10V] | $\eta_c$, 10V [cd/A] | $\lambda_{em}$, 8V [nm] | FWHM$^{*a}$ [nm] | CIE, 8V (x, y) | T$_{75}$ @ 500 nits (h) |
|---|---|---|---|---|---|---|---|
| CBP | 7819 | 13.9 | 50.4 | 510 | 54 | (0.24, 0.62) | 2331 |
| BCzIDQ | 10937 | 15.8 | 60.5 | 514 | 58 | (0.26, 0.66) | 1592 |
| BTPAIDQ | 27662 | 11.6 | 42.1 | 510 | 54 | (0.26, 0.64) | 28 |
| TolCzPhIDQ | 7144 | 9.8 | 36.7 | 512 | 60 | (0.28, 0.64) | 116 |
| Tol2NPhPhIDQ | 21849 | 8.9 | 32.0 | 510 | 56 | (0.27, 0.63) | 85 |
| TolCzdiIDQ | 23150 | 9.8 | 37.0 | 513 | 62 | (0.28, 0.64) | 6 |

$^a$FWHM: full width at half maximum

TABLE 7 properties of green OLED. (device configuration: NPNPB 60/NPB(10)/TCTA(10)/7% Ir(ppy)3:host material(30)/BAlq(30)/LiF(1))

| Device | V, 500 nits | Current density [mA/cm$^2$, 500 nits] | $\eta_{ext}$ [%, 500 nits] | $\eta_c$ [cd/A, 500 nits] | $\eta_p$ [lm/w, 500 nits] |
|---|---|---|---|---|---|
| CBP | 6.9 | 1.213 | 11.4 | 41.1 | 18.5 |
| BCzIDQ | 6.3 | 0.713 | 18.4 | 70.2 | 35.1 |
| BTPAIDQ | 5.6 | 1.079 | 12.6 | 45.9 | 25.7 |
| TolCzPhIDQ | 6.7 | 1.339 | 10.0 | 37.2 | 17.6 |
| Tol2NPhPhIDQ | 5.6 | 1.388 | 10.0 | 35.9 | 20.2 |
| TolCzdiIDQ | 5.7 | 0.969 | 13.9 | 52.2 | 29.1 |

TABLE 8 properties of orange OLED. (device configuration: NPNPB 60/NPB (10)/TCTA (10)/4% Ir (pq)3: host material (30)/BAlq (30)/LiF (1))

| Device | L, 10V [cd/m$^2$] | $\eta_{ext}$ [%, 10V] | $\eta_c$, 10V [cd/A] | $\lambda_{em}$, 8V [nm] | FWHM [nm] | CIE, 8V (x, y) | $T_{75}$ @ 500 nits (h) |
|---|---|---|---|---|---|---|---|
| CBP | 7082 | 12.2 | 37.1 | 580 | 62 | (0.54, 0.46) | 2415 |
| BPhIDQ | 4677 | 16.3 | 44.0 | 584 | 78 | (0.56, 0.44) | 2809 |
| BCzIDQ | 3278 | 14.5 | 40.0 | 582 | 64 | (0.55, 0.45) | 955 |
| BTPAIDQ | 18565 | 10.0 | 27.4 | 582 | 74 | (0.55, 0.74) | 18 |
| TolCzPhIDQ | 6963 | 15.3 | 40.9 | 588 | 76 | (0.57, 0.43) | 2520 |
| Tol2NPhPhIDQ | 18459 | 11.3 | 32.2 | 580 | 72 | (0.55, 0.45) | 472 |

TABLE 9 properties of orange OLED. (device configuration: NPNPB 60/NPB(10)/TCTA(10)/4% Ir(pq)3: host materials(30)/BAlq(30)/LiF(1))

| Device | V, 500 nits | Current density [mA/cm$^2$, 500 nits] | $\eta_{ext}$ [%, 500 nits] | $\eta_c$ [cd/A, 500 nits] | $\eta_p$ [lm/w, 500 nits] |
|---|---|---|---|---|---|
| CBP | 6.7 | 1.156 | 14.1 | 43.1 | 20.3 |
| BPhIDQ | 6.9 | 0.963 | 19.3 | 52.0 | 23.8 |
| BCzIDQ | 8.0 | 1.006 | 16.8 | 49.8 | 19.5 |
| BTPAIDQ | 5.9 | 1.497 | 12.0 | 33.2 | 17.8 |
| TolCzPhIDQ | 6.2 | 1.018 | 18.4 | 49.0 | 24.9 |
| Tol2NPhPhIDQ | 5.6 | 1.340 | 13.0 | 37.1 | 20.8 |

TABLE 10 properties of green OLED. (device configuration: NPNPB 60/NPB (10)/TCTA (10)/4% Ir (piq)3: host material (30)/BAlq (30)/LiF (1))

| Device | L, 10V [cd/m$^2$] | $\eta_{ext}$ [%, 10V] | $\eta_c$, 10V [cd/A] | $\lambda_{em}$, 8V [nm] | FWHM [nm] | CIE, 8V (x, y) | $T_{75}$ @ 500 nits (h) |
|---|---|---|---|---|---|---|---|
| CBP | 1027 | 1.6 | 0.9 | 620 | 52 | (0.62, 0.33) | 97 |
| BPhIDQ | 1635 | 14.4 | 17.8 | 618 | 58 | (0.67, 0.33) | 254 |
| BCzIDQ | 1015 | 12.3 | 16.5 | 616 | 52 | (0.66, 0.34) | 92 |
| BTPAIDQ | 6745 | 13.0 | 15.8 | 620 | 54 | (0.67, 0.33) | 14 |
| TolCzPhIDQ | 2120 | 14.5 | 17.9 | 620 | 60 | (0.67, 0.33) | 222 |
| Tol2NPhPhIDQ | 9645 | 11.9 | 15.7 | 618 | 54 | (0.66, 0.33) | 75 |

TABLE 11 properties of red OLED(device configuration: NPNPB (60)/NPB(10)/TCTA(10)/4% Ir(piq)3:host material(30)/BAlq(30)/LiF(1))

| Device | V, 500 nits | Current density [mA/cm$^2$, 500 nits] | $\eta_{ext}$ [%, 500 nits] | $\eta_c$ [cd/A, 500 nits] | $\eta_p$ [lm/w, 500 nits] |
|---|---|---|---|---|---|
| CBP | 13.3 | 8.396 | 4.7 | 6.0 | 1.4 |
| BPhIDQ | 8.4 | 2.505 | 16.2 | 20.0 | 7.5 |
| BCzIDQ | 9.0 | 2.813 | 13.2 | 17.8 | 6.2 |
| BTPAIDQ | 7.0 | 2.670 | 15.3 | 18.7 | 8.5 |
| TolCzPhIDQ | 7.7 | 2.481 | 16.4 | 20.2 | 8.2 |
| Tol2NPhPhIDQ | 6.7 | 2.702 | 14.0 | 18.5 | 8.7 |

Referring to Table 3 to Table 11, it shows performance of green, orange and red light-emitting devices. It is noted that the red and orange light-emitting device using the compounds of the present invention as host material have longer device life under 500 nit.

In conclusion, the 6H-indeno[2,1-b]quinoline derivative of the present invention is provided with high thermal stability and can be applied in the light-emitting layer of an OLED device to achieve high device performance.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A 6H-indeno[2,1-b]quinoline derivative having a structure of formula (I):

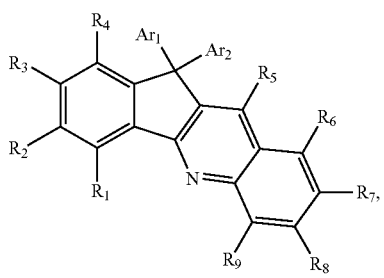

(I)

wherein each of $Ar_1$ and $Ar_2$ is a member selected from the group consisting of a substituted or non-substituted aryl group and a substituted or non-substituted heteroaryl group; each of substituents $R_1$ to $R_9$ is a member independently selected from the group consisting of H, halo, cyano, amino, substituted or non substituted $C_1$-$C_{10}$ alkyl, substituted or non substituted $C_2$-$C_{10}$ alkenyl, substituted or non substituted $C_2$-$C_{10}$ alkynyl, substituted or non substituted $C_3$-$C_{20}$ cycloalkyl, substituted or non substituted $C_3$-$C_{20}$ cycloalkenyl, substituted or non substituted $C_1$-$C_{20}$ heterocycloalkyl, substituted or non substituted $C_1$-$C_{20}$ heterocycloalkenyl, substituted or non substituted aryl and substituted or non substituted heteroaryl.

2. The 6H-indeno[2,1-b]quinoline derivative according to claim 1 having a structure of formula (II):

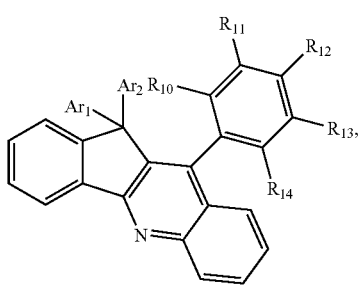

(II)

wherein each of substituents $R_{10}$ to $R_{14}$ is a member independently selected from the group consisting of H, halo, cyano, amino, substituted or non substituted $C_1$-$C_{10}$ alkyl, substituted or non substituted $C_2$-$C_{10}$ alkenyl, substituted or non substituted $C_2$-$C_{10}$ alkynyl, substituted or non substituted $C_3$-$C_{20}$ cycloalkyl, substituted or non substituted $C_3$-$C_{20}$ cycloalkenyl, substituted or non substituted $C_1$-$C_{20}$ heterocycloalkyl, substituted or non substituted $C_1$-$C_{20}$ heterocycloalkenyl, substituted or non substituted aryl and substituted or non substituted heteroaryl.

3. The 6H-indeno[2,1-b]quinoline derivative according to claim 1 having a structure of formula (III):

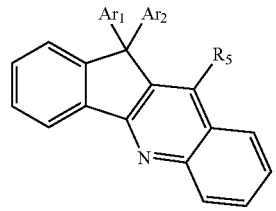

(III)

4. The 6H-indeno[2,1-b]quinoline derivative according to claim 1 having a structure of formula (V):

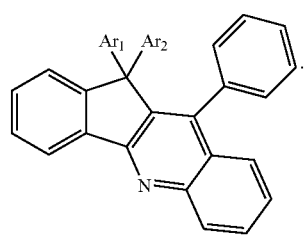

(V)

5. The 6H-indeno[2,1-b]quinoline derivative according to claim 1 having a structure of formula (VI) or formula (VII):

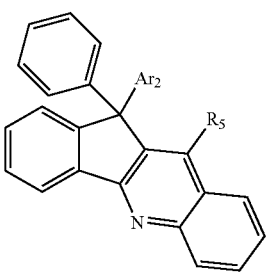

(VI)

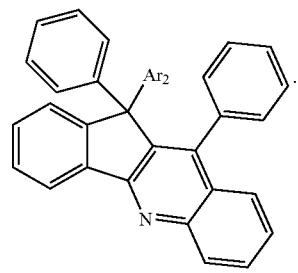

(VII)

6. The 6H-indeno[2,1-b]quinoline derivative according to claim 1 having a structure of formula (VIII) or formula (IX):

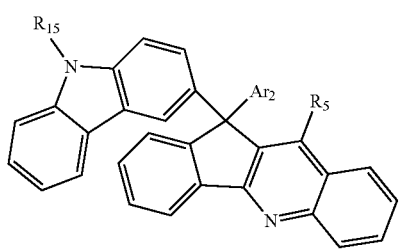

(VIII)

-continued

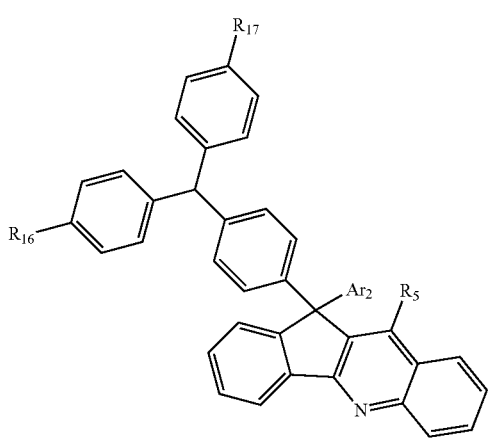

(IX)

wherein each of substituents $R_{15}$ to $R_{17}$ is a member independently selected from the group consisting of H, halo, cyano, amino, substituted or non substituted $C_1$-$C_{10}$ alkyl, substituted or non substituted $C_2$-$C_{10}$ alkenyl, substituted or non substituted $C_2$-$C_{10}$ alkynyl, substituted or non substituted $C_3$-$C_{20}$ cycloalkyl, substituted or non substituted $C_3$-$C_{20}$ cycloalkenyl, substituted or non substituted $C_1$-$C_{20}$ heterocycloalkyl, substituted or non substituted $C_1$-$C_{20}$ heterocycloalkenyl, substituted or non substituted aryl and substituted or non substituted heteroaryl.

7. An organic light emitting diode comprising:
a cathode;
an anode; and
a light-emitting layer arranged between the anode and the cathode, wherein the light-emitting layer comprises a 6H-indeno[2,1-b]quinoline derivativ;
wherein the 6H-indeno[2,1-b]quinoline derivative has a structure of formula (I):

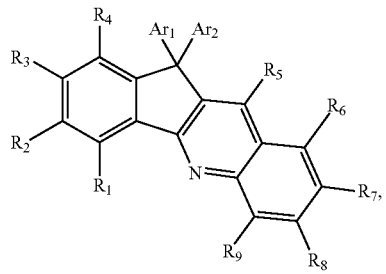

(I)

wherein each of $Ar_1$ and $Ar_2$ is a member selected from the group consisting of a substituted or non-substituted aryl group and a substituted or non-substituted heteroaryl group; each of substituents $R_1$ to $R_9$ is a member independently selected from the group consisting of H, halo, cyano, amino, substituted or non substituted $C_1$-$C_{10}$ alkyl, substituted or non substituted $C_2$-$C_{10}$ alkenyl, substituted or non substituted $C_2$-$C_{10}$ alkynyl, substituted or non substituted $C_3$-$C_{20}$ cycloalkyl, substituted or non substituted $C_3$-$C_{20}$ cycloalkenyl, substituted or non substituted $C_1$-$C_{20}$ heterocycloalkyl, substituted or non substituted $C_1$-$C_{20}$ heterocycloalkenyl, substituted or non substituted aryl and substituted or non substituted heteroaryl.

8. The organic light emitting diode according to claim 7, wherein the 6H-indeno[2,1-b]quinoline derivative has a structure of formula (II):

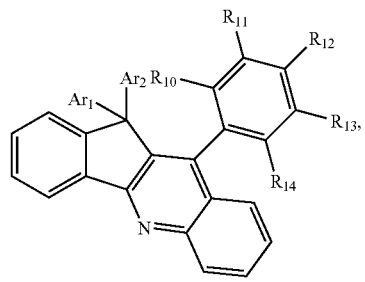

(II)

wherein each of substituents $R_{10}$ to $R_{14}$ is a member independently selected from the group consisting of H, halo, cyano, amino, substituted or non substituted $C_1$-$C_{10}$ alkyl, substituted or non substituted $C_2$-$C_{10}$ alkenyl, substituted or non substituted $C_2$-$C_{10}$ alkynyl, substituted or non substituted $C_3$-$C_{20}$ cycloalkyl, substituted or non substituted $C_3$-$C_{20}$ cycloalkenyl, substituted or non substituted $C_1$-$C_{20}$ heterocycloalkyl, substituted or non substituted $C_1$-$C_{20}$ heterocycloalkenyl, substituted or non substituted aryl and substituted or non substituted heteroaryl.

9. The organic light emitting diode according to claim 7, wherein the 6H-indeno[2,1-b]quinoline derivative has a structure of formula (III):

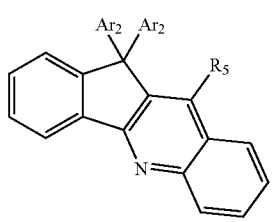

(III)

10. The organic light emitting diode according to claim 7, wherein the 6H-indeno[2,1-b]quinoline derivative has a structure of formula (V):

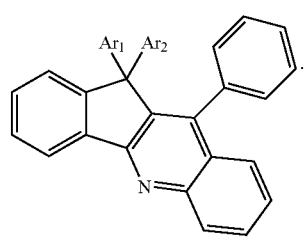

(V)

11. The organic light emitting diode according to claim 7, wherein the 6H-indeno[2,1-b]quinoline derivative has a structure of formula (VI) or formula (VII):

(VI)

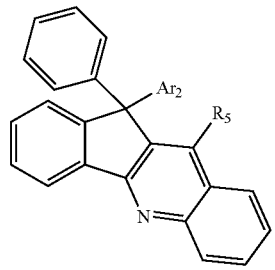

(VII)

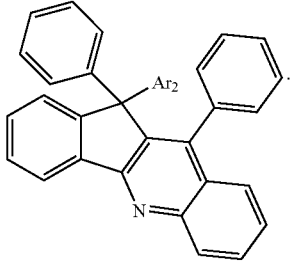

12. The organic light emitting diode according to claim 7, wherein the 6H-indeno[2,1-b]quinoline derivative has a structure of formula (VIII) or formula (IX):

(VIII)

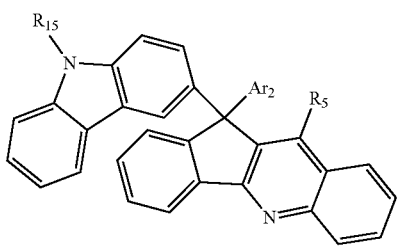

(IX)

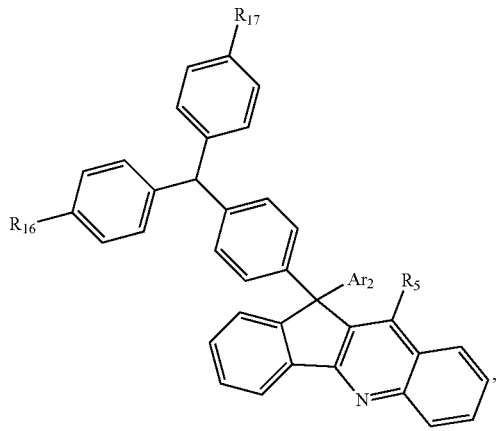

wherein each of substituents $R_{15}$ to $R_{17}$ is a member independently selected from the group consisting of H, halo, cyano, amino, substituted or non substituted $C_1$-$C_{10}$ alkyl, substituted or non substituted $C_2$-$C_{10}$ alkenyl, substituted or non substituted $C_2$-$C_{10}$ alkynyl, substituted or non substituted $C_3$-$C_{20}$ cycloalkyl, substituted or non substituted $C_3$-$C_{20}$ cycloalkenyl, substituted or non substituted $C_1$-$C_{20}$ heterocycloalkyl, substituted or non substituted $C_1$-$C_{20}$ heterocycloalkenyl, substituted or non substituted aryl and substituted or non substituted heteroaryl.

13. The organic light emitting diode according to claim 7, wherein the organic light emitting diode is a red phosphorescent OLED, a green phosphorescent OLED or an orange phosphorescent OLED.

14. The organic light emitting diode according to claim 7, wherein the 6H-indeno[2,1-b]quinoline derivative is a host material or a dopant.

\* \* \* \* \*